(12) United States Patent
Platz

(10) Patent No.: US 7,235,392 B2
(45) Date of Patent: Jun. 26, 2007

(54) APOPTOTIC EBV-TRANSFORMED LYMPHOCYTES, A THERAPEUTIC AGENT FOR POST-TRANSPLANT LYMPHOPROLIFERATIVE DISORDER

(75) Inventor: Matthew S. Platz, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 609 days.

(21) Appl. No.: 10/436,388

(22) Filed: May 12, 2003

(65) Prior Publication Data

US 2004/0005712 A1 Jan. 8, 2004

Related U.S. Application Data

(63) Continuation-in-part of application No. 10/314,869, filed on Dec. 9, 2002.

(60) Provisional application No. 60/379,321, filed on May 10, 2002, provisional application No. 60/338,411, filed on Dec. 7, 2001.

(51) Int. Cl.
*C12N 7/00* (2006.01)
*C12N 5/06* (2006.01)
*G01N 33/00* (2006.01)

(52) U.S. Cl. .................. 435/235.1; 435/326; 435/7.24

(58) Field of Classification Search ...................... None
See application file for complete search history.

(56) References Cited

U.S. PATENT DOCUMENTS

| | | | |
|---|---|---|---|
| 5,945,420 | A | 8/1999 | Araki et al. |
| 6,001,882 | A * | 12/1999 | Fox et al. .................. 514/680 |
| 6,177,441 | B1 | 1/2001 | Cook et al. |
| 6,268,120 | B1 | 7/2001 | Platz et al. |
| 6,503,699 | B1 | 1/2003 | Wollowitz et al. |
| 6,514,987 | B1 | 2/2003 | Cook et al. |
| 6,933,285 | B2 | 8/2005 | Platz et al. |
| 2002/0028432 | A1 | 3/2002 | Cook et al. |
| 2002/0182581 | A1 | 12/2002 | Cook et al. |

OTHER PUBLICATIONS

Fersi, Hannan, M.S., "Binding Affinities of Sensitizers of Pathogen Eradication and Photochemical Behavior of Riboflavin and Riboflavin-N-Oxide," A Thesis, 2002, The Ohio State University.
Brown, J.M., "SR 4233 (Tirapazamine): a new anticancer drug exploiting hypoxia in solid tumours," Br. J. Cancer 67, pp. 1163-1170, 1993, Macmillan Press Ltd.
Daniels, J. Scott et al., "DNA Cleavage by the Antitumor Agent 3-Amino-1,2,4-benzotriazine 1,4-Dioxide (SR4233): Evidence for Involvement of Hydroxyl Radical," J. Am. Chem. Soc., 118, pp. 3380-3385, 1996, American Chemical Society.
Brown, J.M., "Exploiting the hypoxic cancer cell: mechanisms and therapeutic strategies," Molecular Medicine Today, vol. 6, pp. 157-162, London, UK, 2000.
Kelson, Andrew B. et al., "1,2,4-Benzotriazine 1,4-dioxides. An important class of hypoxic cytotoxins with antitumor activity," Anti-Cancer Drug Design, 13, pp. 575-592, Oxford Univ. Press, 1998.
Brown, J.M., "The Hypoxic Cell: A Target for Selective Cancer Therapy—Eighteenth Bruce F. Cain Memorial Award Lecture," Cancer Research, 59, pp. 5863-5870, Stanford, CA, Dec. 1, 1999.
Brown, J.M. et al., "Tirapazamine: laboratory data relevant to clinical activity," Anti-Cancer Drug Design, 13, pp. 529-539, Oxford Univ. Press, 1998.
Evans, James W. et al., "Tirapazamine is Metabolized to Its DNA-damaging Radical byIntranuclear Enzymes," Cancer Research, 58, pp. 2098-2101, Stanford, CA, May 15, 1998.
Daniels, J.S. et al., "Photochemical DNA Cleavage by the Antitumor Agent 3-Amino-1,2,4-Benzotriazine 1,4-Dioxide (Tirapazamine, WIN 59075, SR4233)," The Journal of Organic Chemistry, vol. 63, No. 26, pp. 10027-10030, American Chemical Society, 1998.
Patterson, Laurence H. et al., "Electron Paramagnetic Resonance Spectrometry Evidence for Bioreduction of Tirapazamine to Oxidising Free Radicals Under Anaerobic Conditions," Biochemical Pharmacology, Vo. 60, pp. 1933-1935, Elsevier Science Inc., 2000.
Durandy, A. et al., "Sensitivity of EB virus-induced B cell tumor to apoptosis mediated by anti-CD95/Apo-1 fas antibody," Eur J Immunol, 1997, vol. 27, pp. 538-543.
Buckley, CD, et al. "RGD peptides induce apoptosis by direct caspase-3 activation", Nature, vol. 397, Feb. 11, 1999, pp. 534-538.
Cahir-McFarland, ED et al "NF-kB inihibition causes spontaneous apoptosis in Epstein-Barr virus-transformed lymphoblastoid cells" PNAS, May 23, 2000 vol. 97, No. 11, 6055-6060.
Denny, WA, "The role of hypoxia-activated prodrugs in cancer therapy", Lancelot Oncol. 2000, 1, pp. 25-29.
Kuratomi et al. "Studies on the interactions between DNA and Vlavins", Biocim. Biophys. Acta. 1977, 476, 207-217.
Yoneda, F. et al. "Syntheses of Isoalloxazines and Isoalloxazine 5-Oxides. A New Synthesis of Riboflavin", Jour. Am. Chemical Society, 98:3, Feb. 4, 1976, pp. 830-835.
International Search Report from PCT/US03/14684, Nov. 20, 2003.

* cited by examiner

*Primary Examiner*—Bruce R. Campell
*Assistant Examiner*—Sharon Hurt
(74) *Attorney, Agent, or Firm*—Calfee, Halter & Griswold, LLP

(57) ABSTRACT

Cell preparations comprising a plurality of apoptotic EBV-transformed B lymphocytes and methods of producing cell preparations comprising a plurality of apoptotic EBV-transformed B lymphocytes. The methods comprise transforming B lymphocytes with EBV, incubating the transformed B lymphocytes with a flavin N-oxide photosensitizer, adding a non-toxic antioxidant, and exposing the lymphocytes to an activator, such as photoradiation of an appropriate wavelength to activate the photosensitizer. Also provided are methods of using the apoptotic EBV-transformed B lymphocyte cell preparations to elicit production of EBV-specific T cells in human patients. Finally, methods of treating organ transplant patients, specifically children, comprising administering an effective amount of the apoptotic EBV-transformed B-lymphocyte cell preparation to the patient prior to transplantation are provided.

17 Claims, 4 Drawing Sheets

APOPTOTIC EBV-TRANSFORMED LYMPHOCYTES, A THERAPEUTIC AGENT FOR POST-TRANSPLANT LYMPHOPROLIFERATIVE DISORDER

CROSS-REFERENCE TO RELATED APPLICATIONS

This application is a continuation in part of U.S. patent application Ser. No. 10/314,869, filed Dec. 9, 2002, which claims priority to U.S. Provisional Application Ser. No. 60/338,411, filed Dec. 7, 2001. This application also claims priority to U.S. Provisional Application Ser. No. 60/379,321 filed May 10, 2002, the entirety of which is incorporated herein by reference.

BACKGROUND

Epstein-Barr virus (EBV) is a gamma herpes virus that resides in approximately 85% of adults in the United States. EBV specifically infects human B cells, which in cell culture or in an immune compromised host, will transform to a malignant phenotype and grow without control (i.e., immortalize). Most people acquire EBV sub-clinically, but for some, the initial infection is heralded by infectious mononucleosis. Subsequently, a normal, healthy adult harbors few EBV+ B lymphocytes in the body (so called "latently infected"), and an "army" of EBV-specific T cells that keep the EBV+ B cells "in check" from ever reactivating and causing EBV+ B cell lymphoma in the human for the rest of their life. However, if an individual has suppression of their T lymphocytes, for whatever reason (e.g., congenital, acquired, or iatrogenic immune deficiency that follows solid organ transplantation), endogenous reactivation of the latently infected B cells by the lytic form of EBV can be fatal. Further, in immune suppressed children who have yet to be exposed to EBV, primary infection by the virus during states of iatrogenic immune deficiency such as occurs with immune suppressive therapy for solid organ transplantation is highly fatal. Indeed, 20% of children who undergo liver transplantation die from this complication (i.e., post-transplant lymphoproliferative disorder, or PTLD).

PTLD is highly fatal in children undergoing solid organ transplantation as noted above, and complicates approximately 2% of adult patients undergoing kidney transplantation and up to 20% of cardiac transplants in adults. These patients must take immunosuppressive therapy so they do not reject their transplanted organs. This therapy suppresses T cells that guard against either primary EBV infection or re-infection from latent EBV. PTLD is fatal in approximately 30–50% of cases. For the vast majority of adults, treatment of PTLD consists of reduction in immune suppressive therapy, sometimes followed by immunotherapy or chemotherapy. Reduction in immune therapy is an option in adult transplant patients because adults are previously exposed to EBV and therefore have immunologic memory T cells that can be activated against PTLD once immune suppression is reduced. However, the vast majority of children do not have EBV specific T cells, and in childhood solid organ transplants, the lack of a prior infection/exposure of EBV can lead to a rapid, often fatal complication from EBV-associated PTLD, as noted above. Indeed, some transplantation centers will not allow liver transplantation if a child does not have prior exposure to EBV.

SUMMARY

The present invention provides compositions and methods which use such compositions to prophylactically protect a human subject about to undergo an organ transplant against post-transplant lymphoproliferative disorder (PTLD). In one embodiment the composition is a cell preparation which comprises a plurality of apoptotic EBV-transformed B lymphocytes. Such lymphocytes comprise flavin-DNA adducts. The cell preparation may further comprise an adjuvant. In certain embodiments, the method comprises administering a therapeutically effective amount of this cell preparation or the isolated lymphocytes contained therein to the patient.

In another aspect the method comprises a method of producing a cell preparation which comprises a plurality of apoptotic EBV transformed lymphocytes. The method comprises: transforming B lymphocytes with EBV, incubating said EBV-transformed B lymphocytes in a medium comprising a flavin N-oxide photosensitizer such as riboflavin N-oxide (RBO) or another flavin N-oxide photosensitizer, referred to hereinafter as the "flavin N-oxide photosensitizer" under conditions which permit uptake of the photosensitizer by the lymphocytes, adding a non-toxic antioxidant to the medium; and exposing the cells to photoradiation of an appropriate wavelength or an enzymatic activator to activate the flavin N-oxide. Preferably, at least 25% of the EBV-transformed lymphocytes are in S phase when incubated with the flavin N-oxide; more preferably at least 35% of the EBV-transformed lymphocytes are in the S phase when incubated with the flavin N-oxide; and even more preferably, at least 50% of the EBV-transformed lymphocytes are in the S phase when incubated with the flavin N-oxide. Preferably, the wavelength of light used to activate the flavin N-oxide or flavin N-oxide photosensitizer is in the visible region, i.e., from about 400 to about 700 nm; more preferably, the wavelength is in the range from about 400 to about 500 nm.

The present invention also relates to the cell preparation and the apoptotic cells produced by the present method. Such apoptotic cells comprise flavin N-oxide-DNA adducts.

In another aspect the method comprises eliciting an EBV-specific immune response in vitro or in vivo. The method comprises contacting lymphocytes, particularly T lymphocytes with the apoptotic EBV-transformed B lymphocytes of the present invention. The EBV-transformed B lymphocytes may be purified or partially purified prior to application.

In another aspect, the invention comprises a method of treating an organ transplant patient, particularly someone who is about to undergo an organ transplant, and has little or no circulating levels of EBV-specific T cells. This method is particularly suitable for children who are about to undergo organ transplants. The method comprises administering the present cell preparation in an amount sufficient to elicit production of EBV-specific T-cells in the patient. The cell preparation is preferably administered prior to transplantation and prior to administration of immunosuppressive drugs. Preferably, the cell preparation is administered in an amount sufficient to retard, prevent, or reduce development of post-transplant lymphoproliferative disorder in the patient.

A general structure for flavin N-oxide is shown in formula I:

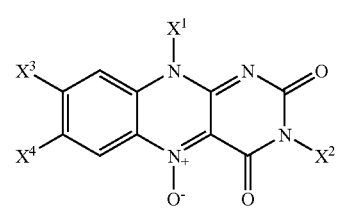

wherein $X^1$ is selected from H, monosaccharides, substitited monosaccharides, mono, di, and tri-ethylene glycol, alcohol, and alkyl ammonium ion; and $X^2$, $X^3$, and $X^4$ can be the same or different and are selected from H, monosaccharides, substitited monosaccharides, glycol, alcohol, lower alkyl, and alkylene groups further substituted with monosaccharides, substitited monosaccharides, mono, di, and tri-ethylene glycol, alcohol, or alkyl ammonium ion.

It is preferred that the substituents are chosen such that the flavin N-oxide is water soluble. One example of a flavin N-oxide is riboflavin N-oxide, which is shown in formula II:

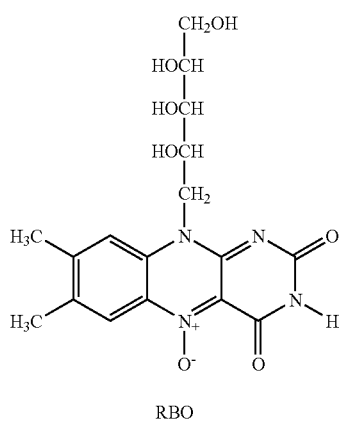

RBO

The method of making the EBV vaccine comprises the steps of a) infecting B lymphocytes with EBV to produce EBV-transformed B lymphocytes, b) incubating the EBV-transformed B lymphocytes in a medium comprising a flavin N-oxide under conditions which permit accumulation of flavin N-oxide in the EBV-transformed B lymphocytes; adding a non-toxic antioxidant to the medium; and exposing the lymphocytes to an activator wherein the flavin N-oxide is activated. It is preferred that the flavin N-oxide used is riboflavin N-oxide. The activator may be electromagnetic radiation, preferably in the visible region, or a reducing enzyme, either from within the cell or from outside of the cell.

When preparing the cell preparation for the vaccine, it is preferred that at least 25% of the EBV-transformed lymphocytes are in the S phase when the flavin N-oxide is added to the medium. The cell preparation prepared by this method comprises a plurality of apoptotic EBV-transformed B lymphocytes, which comprise a DNA-flavin N-oxide adduct. The vaccine comprises the apoptotic EBV-transformed B lymphocytes, which comprise a DNA-flavin N-oxide adduct. The invention still further comprises a method of eliciting production of EBV-specific T-cells in a human subject through the administration of the cell preparation to the subject. Method of eliciting production of EBV-specific T-cells in a human subject through the administration of a purified cell preparation to the subject are also provided.

DETAILED DESCRIPTION

Flavin N-oxides comprise the compound of general formula I:

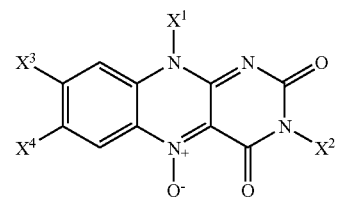

wherein $X^1$ is selected from H, monosaccharides, substituted monosaccharides, mono, di, and tri-ethylene glycol, alcohol, and alkyl ammonium ion; and $X^2$, $X^3$, and $X^4$ can be the same or different and are selected from H, monosaccharides, substitited monosaccharides, glycol, alcohol, lower alkyl, and alkylene groups further substituted with monosaccharides, substitited monosaccharides, mono, di, and tri-ethylene glycol, alcohol, or alkyl ammonium ion.

One example of a flavin N-oxide is riboflavin N-oxide (RBO), which is shown in formula II:

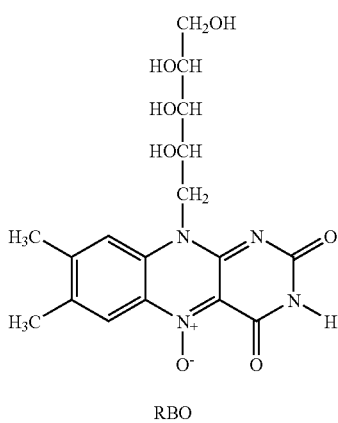

RBO

The flavin N-oxides used in accordance with the present invention are preferably water soluble. Preferably, the solubility of the flavin N-oxides is 100 micromolar or greater. It is desirable to use a water-soluble sensitizer in the preparation of an EBV vaccine, so that the sensitizer can be added to the cell composition without extensive preparation. It is also preferred, but not essential, that the compounds used are electrically neutral to ease transport into cells. In some embodiments, electrically charged species, such as ammonium salts may be used.

Figure 1:
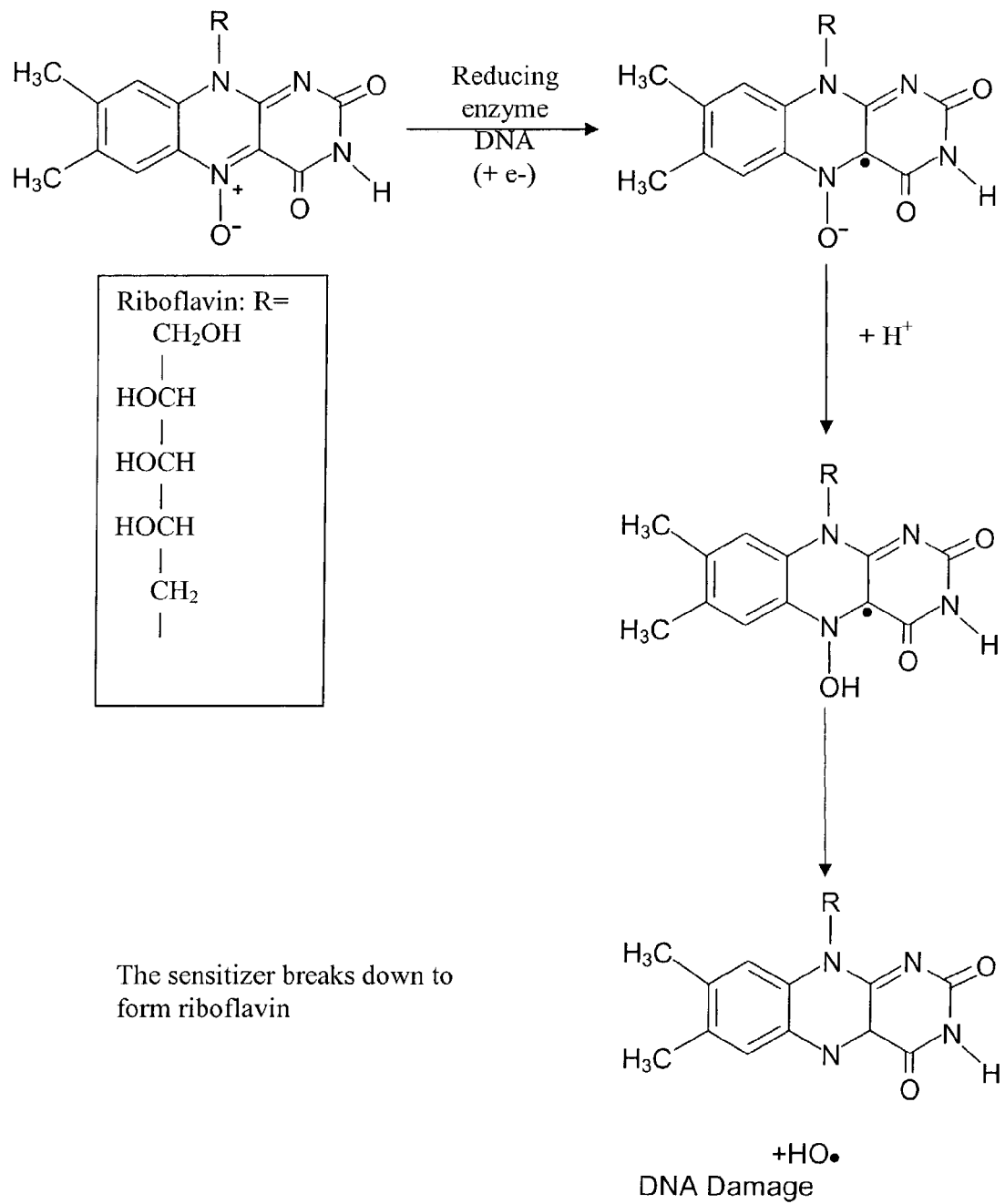
FIG. 1 shows the mechanism of flavin N-oxide activation and decomposition into a molecule of the flavin and a hydroxyl radical.

Riboflavin N-oxide is an example flavin N-oxide, which is both water soluble and electrically neutral. Upon fragmentation of the neutral radical, riboflavin N-oxide forms the hydroxyl radical, which damages the nucleic acid, and riboflavin (vitamin B2) which is generally regarded as safe. A proposed mechanism for the formation of hydroxyl radical is shown FIG. 1.

As shown in the mechanism, the flavin N-oxides react with an activator, i.e. electromagnetic radiation or reducing enzymes, within cells or from outside of cells to form a radical anion. This radical anion, then, when in contact with an acidic complex, is protonated. This converts the radical to a neutral radical, which fragments. The fragmentation results in the formation of a flavin and hydroxyl radical. The hydroxyl radical damages the nucleic acid. When the flavin is riboflavin N-oxide, the flavin formed is riboflavin, vitamin B2, which is generally regarded as safe. Since the acidic complexes in the cells are generally DNA complexes, such as spermidine-DNA complexes, the hydroxyl radical is formed very close to the DNA, which is very effective in damaging one or both strands of the DNA. Comparatively, if the activation occurred far from the DNA, the hydroxyl radical may react with something else before it reaches the DNA. Furthermore, it is believed that these complexes tend to cluster together on a strand of DNA, which results in more severe damage, including more breaks overall and more double-strand breaks, which the cell is unlikely to be able to repair.

When the activator is a reducing enzyme, it is generally an enzyme that is found inside the cell, though it can be a reducing enzyme from outside of the cell. When the activator is electromagnetic radiation, the wavelength will be chosen depending on such factors as the medium the cells is in. Preferably, the wavelength will be a visible wavelength.

Method of Preparing an EBV Vaccine. Method of Producing Apoptotic EBV-transformed Lymphocytes In one aspect, the present invention provides a method of producing apoptotic EBV-transformed B lymphocytes. Such method comprises infecting B lymphocytes that have been obtained from a subject with EBV, incubating the EBV transformed B lymphoctyes with a flavin N-oxide under conditions which permit the flavin N-oxide to enter the B lymphocyte and bind to nucleic acid molecules in the cell, adding a non-toxic anti-oxidant to the incubation medium, and exposing the cells to an activator. The activator may be electromagnetic radiation of an appropriate wavelength to activate the flavin N-oxide or it may be a reducing enzyme that is already present in the cell preparation. The reducing enzyme may either be present in the cell, or may be a reducing agent outside of the cell.

Infection and Transformation of Lymphocytes with EBV Lymphocytes are obtained from a human subject, preferably from a human subject who is about to undergo an organ transplant, using techniques known in the art. Although not necessary, the lymphocytes may be separated into specific B cell and T cell populations prior to exposure to EBV. The B lymphocytes which contain receptors for EBV are then infected with EBV using methods known in the art and maintained in culture. In the infected B lymphocyte, the EBV genome is replicated by cellular DNA polymerase during S phase and persists as multiple extrachromosomal double-stranded DNA EBV episomes. EBV episomes are also known to integrate into chromosomal DNA in latently infected cells. When grown in vitro, the EBV infected B lymphocytes undergo transformation. Such EBV transformed B lymphocytes comprise EBV-specific antigens which may be detected with antisera.

Figure 2:
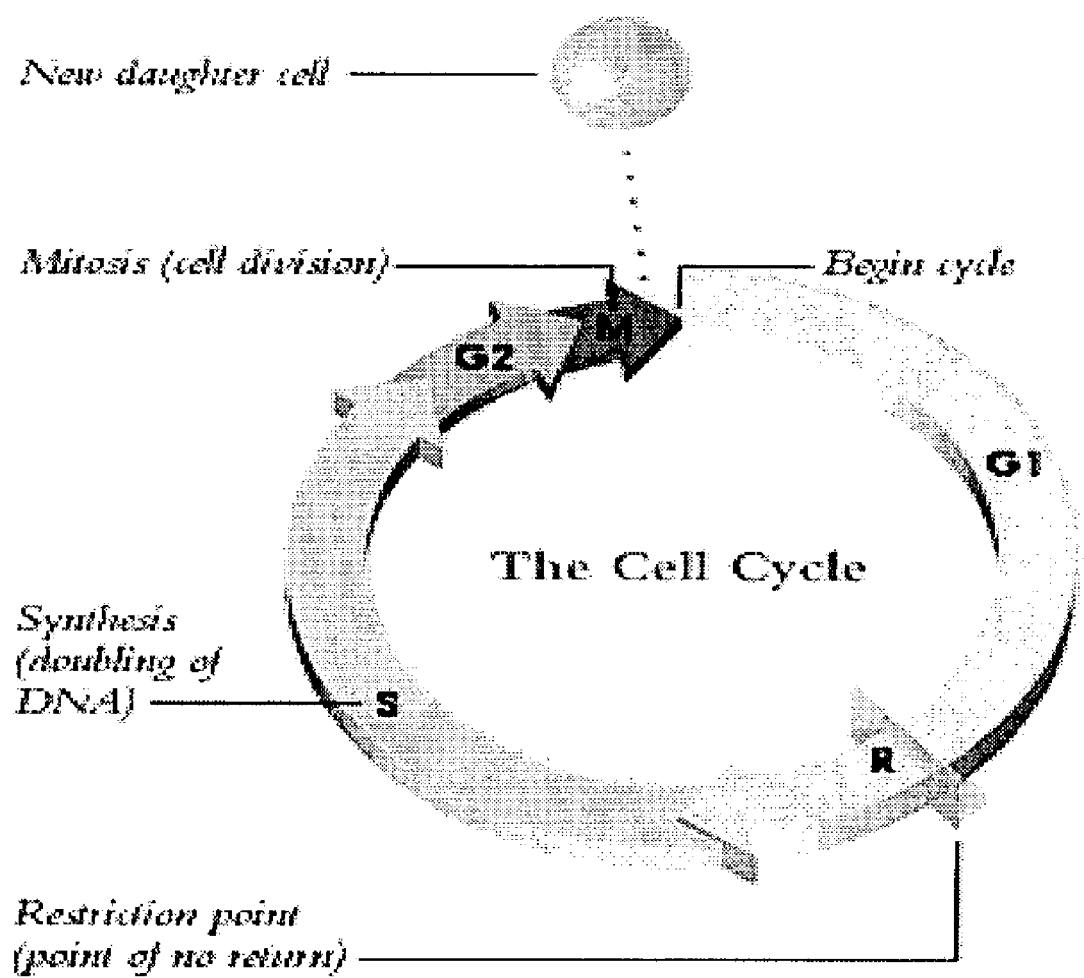
FIG. 2 depicts the cell cycle.

Flavin N-oxide Activation Flavin N-oxides act as photosensitizers. Photosensitizer photophysics and photochemistry is usefully summarized with the aid of the Jablonski diagram (as shown in FIG. 2). The sensitizer in its ground electronic state is referred to as $S_0$. Upon absorption of light it is converted to an electronically excited state, which in condensed phase immediately ($<<10^{-11}$s) relaxes to the lowest vibrational level of the lowest excited state ($S_1$). The lifetimes of $S_1$ states in solution are usually in the range of 1–10 ns and are controlled by internal conversion (IC) and fluorescence (F) decay back to $S_0$, by intersystem crossing (ISC) to a paramagnetic triplet state ($T_1$) and by inter and intramolecular chemical reactions. Because $S_1$ is short-lived, bimolecular reactions of $S_1$ will be inefficient unless the trapping agent is rather concentrated (0.1–1.0 M) or the sensitizer and the trap are complexed. A sensitizer bound to protein or nucleic acid will likely react in its $S_1$ state. Common reactions of $S_1$ are electron transfer and cycloaddition. Fluorescence quenching is characteristic of bimolecular reactions of $S_1$.

Photolysis of flavin N-oxides in their ground singlet states ($S_0$) form an excited singlet state ($S_1$). This state can fragment and fluoresce or relax to its triplet state ($T_1$). The lifetime of triplet states is generally several orders of magnitude greater than the lifetime of singlet states. Triplet states can be detected by laser flash photolysis experiments, the $\lambda_{max}$ is readily determinable by those of skill in the art. Triplet states can also be detected by their phosphorescence and EPR spectra at 77 K.

Electron rich amino acids (tryptophan, tyrosine, histidine and methionine) and nucleotides (guanosine and adenosine monophosphate) quench the fluorescence of RNO. The $S_1$ state of riboflavin N-oxide accepts an electron from the amino acid or nucleotide donor to form a flavin N-oxide radical anion. Electron transfer proceeds on ultrafast time scales upon excitation of flavin N-oxide adenine mononucleotide (FAD) and enzyme bound flavin N-oxides.

In the present embodiment the infected EBV transformed lymphocytes are incubated with a flavin N-oxide. An example of such photosensitizer is shown below:

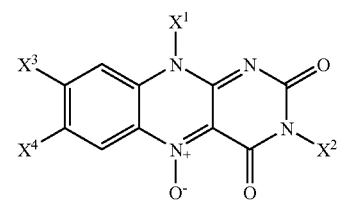

wherein $X^1$ is selected from H, monosaccharides, substitited monosaccharides, mono, di, and tri-ethylene glycol, alcohol, and alkyl ammonium ion; and $X^2$, $X^3$, and $X^4$ may be the same or different and are selected from H, monosaccharides, substitited monosaccharides, glycol, alcohol, lower alkyl, and alkylene groups further substituted with monosaccharides, substitited monosaccharides, mono, di, and tri-ethylene glycol, alcohol, or alkyl ammonium ion. Riboflavin N-oxide is an especially preferred compound for use with the method of the present invention.

Incorporation of the Flavin N-Oxide Photosensitizer into the Cells The EBV-transformed B lymphocytes are incubated in medium containing the flavin N-oxide under conditions that permit accumulation of the flavin N-oxide in the transformed lymphocytes and binding to cellular DNA. The cells, which have accumulated the flavin N-oxide therein are hereinafter collectively referred to as "flavin N-oxide EBV-transformed cells." Following activation these cells contain metabolic breakdown products of the flavin N-oxide and are collectively referred to hereinafter as "flavin N-oxide-sensitized EBV-transformed cells." To enhance binding to cellular DNA, it is preferred that the a substantial portion, i.e., greater than 25%, preferably greater than 35%, more preferably greater than 50% of the EBV-transformed lymphocytes in the cell sample be in S phase. During the S Phase, the cell is actively undergoing DNA synthesis. At the end of the S phase, and just before cell division, it will contain two sets of DNA. It is proposed that cells will be most likely to bind the flavin N-oxide and to undergo the desired flavin N-oxide DNA photochemistry at this point of their cycle. Synchronizing the cells present in the sample maximizes the number of cells in S Phase, and thereby minimizes the quantity of riboflavin N-oxide free in solution, and the risk of toxic cell death, i.e., necrosis.

Synchronization of the cells may be achieved with a drug, such as aphidicolin, which is a DNA polymerase inhibitor. This drug prevents the cells from entering S-phase, the phase during which the cells replicate their DNA. In the presence of aphidicolin those cells already in the posterior phases are killed and the remaining cells accumulate at the beginning of the S phase. The effects of aphidicolin are reversible. The cells start growing and dividing soon after the drug is removed by washing (during washing the cells are concentrated by centrifugation, the supernatant is discarded and the cells are resuspended in non-treated media.).

The amount of flavin N-oxide incorporated into the medium is an amount sufficient to induce apoptosis of the flavin N-oxide sensitized EBV-transformed lymphocytes. As taught herein, optimal concentrations may be readily determined by those skilled in the art without undue experimentation. Preferably, the smallest efficacious concentration of flavin N-oxide is used.

Apoptosis is a highly ordered genetically programmed cell death, which results in DNA degradation and nuclear condensation. It is activated by internal signals from the cell itself. In contrast, necrosis is death due to external injury to the cells. Cellular necrosis is a form of cell death that involves a swelling of the cells and membrane rupture. Apoptotic cell death is typically accompanied by one or more characteristic morphological and biochemical changes in cells, such as condensation of cytoplasm, loss of plasma membrane microvilli, segmentation of the nucleus, degradation of chromosomal DNA or loss of mitochondrial function. A recognized biochemical marker of apoptosis is the cleavage of chromatin into nucleosomal fragments. During apoptosis, cells may present signals, which may be used to induce significant immune responses. Levels of apoptosis and necrosis of the RBO-sensitized EBV-transformed lymphocytes may be determined via flow cytometry using a technique described by Vermes[4].

In the process of apoptosis, many changes occur in the cell. One of these changes is the translocation of phophatidylserine from the inside face of the plasma membrane to the outside. This change may be detected using a probe which has high affinity to phosphatidylserine called Annexin V. If Annexin V is complexed to a fluorochrome, such as fluorescien isothiocyanate (FITC), it may be detected by a flow cytometer.

The translocation of phosphatidylserine also occurs as a result of necrotic cell death, however. One distinction between apoptotic cell death and necrotic cell death is that during the early stages of apoptosis, the outer membrane of the cell remains intact. After necrosis occurs, the membrane becomes leaky and allows substances to pass through. Consequently, one may use the fluorescent dye DNA stain propidium iodide (PI), which only passes through leaky membranes, as a membrane exclusion dye. In this way, only necrotic cells which allow PI to pass through will be PI positive, while normal and apoptotic cells will be PI negative.

In summary, using Annexin V-PI staining, if cells are normal they will be negative for Annexin V and negative for PI staining. If cells are apoptotic, they will be positive for Annexin V and negative for PI. If cells are necrotic, they will be positive for both Annexin V and PI. This is represented by a flow cytometer as a density plot (note that each point represents a cell, whose X coordinate is a function of how much Annexin V is detected on the cell and whose Y coordinate is a function of how much PI is detected in the cell). Other examples of assays for apoptosis follow.

Comet (Single-Cell Gel Electrophoresis) Assay to Detect Damaged DNA The Comet assay, or single-cell gel electrophoresis assay, is used for rapid detection and quantitation of DNA damage from single cells. The Comet assay is based on the alkaline lysis of labile DNA at sites of damage. Cells are immobilized in a thin agarose matrix on slides and gently lysed. When subjected to electrophoresis, the unwound, relaxed DNA migrates out of the cells. After staining with a nucleic acid stain, cells that have accumulated DNA damage appear as bright fluorescent comets, with tails of DNA fragmentation or unwinding. In contrast, cells with normal, undamaged DNA appear as round dots, because their intact DNA does not migrate out of the cell.

TUNEL Assay When DNA strands are cleaved or nicked by nucleases, a large number of 3'-hydroxyl ends are exposed. In the TUNEL assay (terminal deoxynucleotidyl transferase dUTP nick end labeling), these ends are labeled with UTP using mammalian terminal deoxynucleotidyl transferase (TdT), which covalently adds labeled nucleotides to the 3'-hydroxyl ends of these DNA fragments in a template-independent fashion. The UTP is then detected using specific probes (e.g., you may incorporate BrdUTP and then use a fluorescent anti-BrdU antibody). The assay may be used on cells in situ or the cells may be analyzed by flow cytometry.

Apoptosis Assays Using Annexin V Conjugates The human anticoagulant annexin V is a 35–36 kilodalton, $Ca^{2+}$-dependent phospholipid-binding protein that has a high affinity for phosphatidylserine (PS). In normal viable cells, PS is located on the cytoplasmic surface of the cell membrane. However, in apoptotic cells, PS is translocated from the inner to the outer leaflet of the plasma membrane, where it is associated with lipid "rafts"—regions of the plasma membrane that are insoluble in detergents, high in cholesterol and sphingolipids, that sequester glycosylphosphatidylinositol (GPI)-linked proteins and tyrosine-phosphorylated proteins and that seem to be involved in signal transduction. Annexin V that is conjugated to various detectable molecules (i.e., fluorescent molecules) are reacted with cells thought to be undergoing apoptosis. If PS is located on the outer surface of the plasma membrane, the annexin V conjugate will bind and be detectable.

Apoptosis Assays Based on Protease Activity Members of the caspase (CED-3/ICE) family of proteases are crucial mediators of the complex biochemical events associated with apoptosis. In particular, caspase-3 (CPP32/apopain), which has a substrate specificity for the amino acid sequence Asp-Glu-Val-Asp (DEVD), cleaves a number of different proteins, including poly(ADP-ribose) polymerase (PARP), DNA-dependent protein kinase, protein kinase, and actin. Procaspase-3 is released from the mitochondria into the cytoplasm during apoptosis and activated to caspase-3 by an as-yet-unknown enzyme. Assays for caspase comprise addition of substrates for the enzyme that, for example, increase their fluorescence upon cleavage by caspase 3.

Addition of a Non-toxic Antioxidant To reduce or prevent nonspecific cellular damage, i.e., damage to the cell membrane rather than the DNA, of the EBV-transformed B lymphocytes from photolysed breakdown products the flavin N-oxide, and thereby favor cellular apoptosis as opposed to cellular necrosis, a non-toxic antioxidant is added to the medium of the EBV-transformed B lymphocytes. As used herein the term "non-toxic antioxidant" refers to a compound, preferably a physiological compound, that, at concentrations which are non-toxic to cells, is capable of reducing or inhibiting formation of the long-lived oxidants that are formed when the flavin N-oxide is exposed to visible light. The non-toxic antioxidant is added to the medium prior to irradiation of the flavin N-oxide treated EBV-transformed B lymphocytes. When a reducing enzyme is used as activator, the non-toxic antioxidant may be added with the flavin N-oxide. Thus, the non-toxic antioxidant may be added concurrently with the flavin N-oxide or following accumulation, i.e., equilibration, of the flavin N-oxide in the cell.

The amount of non-toxic antioxidant used depends on the concentration of the flavin N-oxide, and amount of light exposure. As used herein the term "non-toxic antioxidant" refers to a compound, preferably a physiological compound, that, at concentrations which are non-toxic to cells, is capable of reducing or inhibiting formation of the long-lived oxidants that are formed when RB or the LC-resistant flavin photosensitizer is exposed to visible light. "Non-toxic to cells" means that cell death or prevention of cell growth are minimized or avoided altogether. The non-toxic antioxidant is added to the medium prior to photoradiation of the flavin N-oxide treated EBV-transformed B lymphocytes. Thus, the non-toxic antioxidant may be added concurrently with the flavin N-oxide photosensitizer or following accumulation, i.e., equilibration, of the flavin N-oxide photosensitizer in the cell. The amount of non-toxic antioxidant to be added can readily be determined by those skilled in the art. Glutathione is one antioxidant that has been found particularly useful for the present application.

Activation of the Flavin N-oxide treated EBV-Transformed Lymphocytes After treating the EBV-transformed B lymphocytes with the flavin N-oxide sensitizer, the sensitizer must be activated in order for it to release the hydroxyl radical. The sensitizer is preferably activated with a reducing enzyme. Preferably the reducing enzyme will be one that is present in the cells, though it may be a reducing agent outside of the cell.

Photoradiation of the Flavin N-oxide Treated EBV-Transformed Lymphocytes Alternatively, the flavin N-oxide treated EBV-transformed B lymphocytes are exposed to electromagnetic radiation of the appropriate wavelength to activate the flavin N-oxide photosensitizer. The electromagnetic radiation should be sufficient to activate the flavin N-oxide photosensitizer, but less than that which would cause substantial non-photosensitizer sensitized damage to the biological components of the cell. The wavelength of light used and the amount of radiation used is readily determinable without undue experimentation by one of ordinary skill in the art, using literature sources or direct undue experimentation by one of ordinary skill in the art, using literature sources or direct measurement. Preferably the source of the electromagnetic radiation is a visible light source providing 400 nm to about 700 nm, and more preferably about 400 nm to about 500 nm light. All other parameters that may be involved in preparing a cell preparation comprising a plurality of apoptotic EBV-transformed lymphocytes, including appropriate temperatures for the incubation and photoradiation steps as well as the ranges of temperature, intensity and duration of exposure to electromagnetic radiation, and photosensitizer and non-toxic antioxidant concentrations which will optimize apoptosis and minimize damage to EBV proteins and the cellular membrane also easily determined as is known in the art or readily determinable without undue experimentation by one of ordinary skill in the art, using literature sources or direct measurement.

Purification of the Cell Preparation In addition to the apoptotic EBV-transformed lymphoctyes, the cell preparation further comprises metabolic breakdown products of the flavin N-oxide photosensitizer. If desired, these breakdown products may be substantially removed from the preparation using standard techniques to provide a partially purified preparation of in activated EBV-transformed cells. For example, the photosensitized cell preparation may be subjected to low speed centrifugation to pellet the cells. The supernatant, which contains the extracellular metabolic breakdown products, is discarded and the cells collected. Additional washing steps with fresh medium may be used to remove residual extracellular materials and to further purify the cell preparation.

Furthermore, it is believed that these compositions will be very safe for human subjects. For example, prematurely born infants often have immature livers that may not degrade bilirubin (BR), a metabolite of hemoglobin, to smaller, more water soluble compounds which can then be excreted. These jaundiced infants are commonly treated by exposure to visible light (447 nm). BR in superficial tissues of neonates absorbs the radiation and forms excited triplet states. The bilirubin triplet state sensitizes the formation of singlet oxygen, and the singlet oxygen so formed attacks and degrades ground state BR to smaller, more water soluble molecules. Riboflavin circulating in the blood of neonates strongly absorbs visible light and is also excited when neonates are treated for hyperbilirubinaemia. Consequently, the blood level of riboflavin in neonates treated with phototherapy is dramatically depleted. The fate of the missing riboflavin is not known with certainty, but some riboflavin is likely converted to lumichrome and to albumin adducts in the neonates. Since the sensitizers of the present invention break down to hydroxyl radical and riboflavin, they are expected to be safe for use in humans.

There is a hereditary trait common, but not limited to people of Amish descent known as Crigler-Najjar Syndrome. These individuals cannot degrade BR and undergo BR (and inadvertently riboflavin) phototherapy throughout their lives, or until liver transplantation is possible. No unusual health effects have been observed as a consequence of long term phototherapy, the photolysis of riboflavin in their blood and their subsequent long-term exposure to riboflavin breakdown products. One individual has received whole body phototherapy from birth for over ten years without apparent, unusual health concerns.

Studies in Denmark have considered the possibility that bilirubin (and inadvertently riboflavin) phototherapy might promote cancer. Consequently, they followed over 50,000 neonates receiving BR phototherapy for decades. The number of cancers predicted for this cohort was 85. A total of 87 cancers were found upon cross checking this group against the national cancer registry of Denmark, a result which was considered statistically insignificant. In contrast, it has been concluded that psoralen and UVA phototherapy (PUVA) of psoriasis and subcutaneous lymphoma leads to statistical increases in squamous cell carcinoma (SSC). Extensive experience with riboflavin phototherapy under conditions relevant to blood banking indicates that riboflavin, and thus riboflavin N-oxide and other flavin N-oxides, photolysis in vivo does not lead to increased incidence of cancer. In conclusion, these studies indicate that photolysis-induced breakdown products of riboflavin or riboflavin N-oxide and other flavin N-oxides are not harmful to human subjects. Thus, it is expected that the cell preparations prepared as described above may be used without further purification.

Uses of the Cell Preparations The "non-purified" and partially-purified cell preparations may be used to elicit an immune response either in vitro or in vivo and to treat human subjects, particularly children, who are candidates for an organ transplant. Preferably, the cell preparations that are used to treat organ transplant candidates comprise autologous apoptotic EBV-transformed lymphocytes.

Eliciting an Immune Response in Vitro The cell preparation or the isolated cells contained within the preparation are contacted with peripheral blood under conditions that permit activation and/or proliferation of T lymphocytes.

Eliciting an Immune Response in Vivo A therapeutically effective amount of the cell preparation or the partially purified preparation of flavin N-oxide sensitized EBV-transformed B cells is administered to a human subject, preferably to subject who has little to no circulating levels of EBV-specific T cells. The cell preparation is said to be administered in a "therapeutically effective amount" if the amount administered is physiologically significant. An agent is physiologically significant if its presence results in a detectable change in the physiology of a recipient mammal. In particular, a cell preparation of the present invention is physiologically significant if its presence invokes a cellular immune response in the recipient mammal. This amount is determined using standard techniques. Preferably, this amount is determined by measuring the levels of circulating T cells specific against EBV.

The partially purified or non-purified cell preparation may be combined in admixture with an pharmaceutically acceptable carrier or diluent. Optionally, the partially purified or non-purified cell preparation may be prepared in admixture with an adjuvant. The term "adjuvant" as used herein refers to a compound or mixture that enhances the immune response to an antigen. Adjuvants include, but are not limited to, complete Freund's adjuvant, incomplete Freund's adjuvant, saponin, mineral gels such as aluminum hydroxide, surface active substances such as lysolecithin, pluronic polyols, polyaninons, peptides, oil or hydrocarbon emulsions, keyhole limpet hemocyanins, dinitrophenol, and potentially useful human adjuvants such as BCG (bacille Calmette-Guerin) and *Corynebacterium parvum*. Selection of an adjuvant depends of the animal subject to be vaccinated. Preferably, a pharmaceutically acceptable adjuvant is used. For example, oils or hydrocarbon emulsion adjuvants should not be used for human. One example of an adjuvant suitable for use with humans is alum (alumina gel.)

Preferably, the cell-based immunogenic compositions are administered to the human subject by injection, such as for example intramuscular (i.m.), intradermal (i.d.), intranasal (i.n.) or sub-cutaneous (s.c.) injection. It is contemplated that 2 or more injections over an extended period of time will be optimal. Preferably, the immunogenic compositions are administered in a dosage sufficient to prevent, reduce or retard development of PTLD in a subject through a series of immunization challenge studies using a suitable animal host system, e.g. transgenic mice which are thought to be an acceptable standard for human use considerations.

The dosage to be administered depends on the size of the subject being treated as well as the frequency of administration and route of administration. Ultimately, the dosage will be determined using clinical trials. Initially, the clinician will administer doses that have been derived from animal studies.

Preferably, the cell preparation is administered to the subject prior to organ transplantation and initiation of immunosuppressive medications.

EXAMPLES

Example 1

Flavin N-oxide binding affinities The binding affinity of the flavin N-oxide and two other common sensitizers, AMT and methylene blue, for cellular and plasma components, may be surveyed and compared using a simple two chamber dialysis assay. In chamber 1 is placed a macromolecule such as bovine albumin, calf thymus DNA, phosphatidylserine (which has a net negative charge) or phosphatidylcholine, which has no net charge. The sensitizer is placed in the second chamber and its absorbance is recorded. The two chambers are separated by a semi-permeable membrane with a molecular weight cut of 3500 amu, which permits diffusion of only the sensitizer. If there is no binding of sensitizer to macromolecule the absorbance of chamber 2 will drop by 50% at equilibrium. Binding is demonstrated by a decrease in the absorbance of the sensitizer in chamber 2 of greater than 50%.

In this application human apoptosis and inactivation of EBV-transformed B lymphocytes is effected by selective sensitization of damage to the cellular nucleic acid. Thus, it is highly preferred that the sensitizer recognize chemical differences between the different components of the cell. Preferably, the flavin N-oxide is the sensitizer most likely to associate selectively in the nucleic acid of the cell.

Flavin N-oxides, methylene blue and AMT are all water soluble. Methylene blue and AMT achieve water solubility by the presence of a positive charge. Flavin N-oxides are fundamentally different as they are electrically neutral. Because flavin N-oxides are uncharged they have the greater likelihood of passive transport through membranes and reaching the nucleic acid target of the pathogen.

Example 2

Flavin N-oxide Sensitized Killing of Human Lymphoblastoid Cells Infected with the Epstein Barr Virus Photolysis of the flavin N-oxide (25–100 µL) in aerated RPMI growth medium produces hydrogen peroxide. The yield of hydrogen peroxide correlates with the concentration of flavin N-oxide and the length of exposure of the sample to light.

EBV infected human lymphoblastoid cells (LCLs) are added to commercial solutions of RPMI growth medium that has been previously photolyzed in the presence of the flavin N-oxide. The cells are incubated for 24 hours and then analyzed by cell counts using a hemacytometer with Trypan Blue staining. Photolysis of an RPMI solution that does not contain any flavin N-oxide is used as a control.

We have found that these cells grow normally in the presence of 10 mM glutathione, a physiological antioxidant. Solutions of the flavin N-oxide (100 µM) and glutathione (10 mM) are photolyzed. Cells ($0.50 \times 10^6$ cells/mL) are added to these photolyzed solutions, incubated and counted after 24 hours. A control group of cells is incubated in unphotolyzed RPMI growth medium. From this experiment, it can be shown that glutathione neutralizes the long-lived oxidants produced on photolysis of the flavin N-oxide.

Finally, LCLs are photolyzed in the presence of both 100 µM of the flavin N-oxide and 10 mM glutathione, incubated and counted after 24 hours.

These experiments show that there are essentially two distinct mechanisms of cell death during photolysis of the flavin N-oxide. The first is a nonspecific damage from photolysed breakdown products from the flavin N-oxide which may be neutralized by the addition of an antioxidant such as glutathione. This is represented in our system by photolysis of solutions before the addition of cells. The second is a specific killing associated with damage due to photolysis of the flavin N-oxide directly complexed to human LCLs and quite possibly to their cellular DNA, which would be less susceptible to inhibition by the addition of an antioxidant. We can study this method of killing in our system with photolysis of solutions in the presence of the cells. In this way, we are able to use glutathione to focus on the second more specific form of cell killing.

Example 3

Optimization of the Photolysis A. Glutathione efficiency: This experiment is performed to see if the amount of glutathione could be reduced without reducing the efficiency of the protection against the ROS.

Seven 5-mL solutions of media +100 µM of the flavin N-oxide containing different concentrations of glutathione are photolyzed for 2 hours, then added to $3.5 \times 10^6$ healthy cells ($0.7 \times 10^6$ cells/mL) and put in the incubator for 24 hours.

| Solutions: | # 1 = media alone |
| --- | --- |
| | # 2 = media + 100 µM flavin N-oxide |
| | # 3 = media + 100 µM flavin N-oxide + 0.1 mM of glutathione |
| | # 4 = media + 100 µM flavin N-oxide + 0.5 mM of glutathione |
| | # 5 = media + 100 µM flavin N-oxide + 1 mM of glutathione |
| | # 6 = media + 100 µM flavin N-oxide + 5 mM of glutathione |
| | # 7 = media + 100 µM flavin N-oxide + 10 mM of glutathione |

Cells counts are measured 24 hours after the photolysis of the solutions.

Flavin N-Oxide efficiency: 5 different concentrations of the flavin N-oxide (and one negative control) in media are tested in their ability to kill the cells upon photolysis.

| Solutions: | # 1 contains no flavin N-oxide |
| --- | --- |
| | # 2 contains 10 µM flavin N-oxide |
| | # 3 contains 25 µM flavin N-oxide |
| | # 4 contains 50 µM flavin N-oxide |
| | # 5 contains 75 µM flavin N-oxide |
| | # 6 contains 100 µM flavin N-oxide |

$3.5 \times 10^6$ cells are put into each well ($0.7 \times 10^6$ cells/mL, 5 mL of solution) and allowed to equilibrate for 24 hours in the incubator. The glutathione will be added just before the photolysis. Then, the cells are photolyzed for 2 hours, under the 6 bulbs, and they are left in the incubator overnight. Cells counts are measured after 24 hours in the incubator.

Flavin N-Oxide Equilibration Time To test whether it is possible to reduce equilibration time without altering the efficiency of the incorporation of the flavin N-oxide into the DNA several time points can be tested. Preferably, four time points are tested: 1 h, 2 h, 3 h, and 4 h of equilibration of the cells in a solution containing the flavin N-oxide. The experiment is done with 3 different concentrations of the flavin N-oxide (0 µM as a control, 100 and 50 µM). Thus, 12 flasks containing 7 millions cells in 10 mL of media are prepared. The cells are counted before photolysis and after equilibration.

10 mM of glutathione is added to each flask and the cells are then photolyzed for 2 hours under the 6 bulbs (163.57 lux). They are then left in the incubator for 24 h. The cells are counted after incubation.

Flavin N-Oxide efficiency/equilibration time: 4 different concentrations of flavin N-oxide (0, 10, 25, 50 µM) and 2 equilibration time points are tested. The cells are counted before photolysis and after equilibration.

10 mM of glutathione is added to each flask and the cells are photolyzed for 2 hours. Then they are left in the incubator overnight. The cells are counted after incubation.

Photolysis time: This work is performed at the same time as the other experiments, so the concentration tested is still 50 µM and the equilibration time 24 h. The cells treated with the flavin N-oxide are photolyzed for 2 hours, and will to optimize the photolysis time.

Six flasks containing $7 \times 10^6$ cells in 10 mL of flavin N-oxide-RPMI solution are photolyzed for different times:

=50 gM flavin N-oxide; 30 minutes
2=SO gM flavin N-oxide; 60 minutes
3=100 gM flavin N-oxide; 60 minutes
4=100 gM flavin N-oxide; 0 minutes
5=0 gM flavin N-oxide (RPMI only); 0 minutes
6=0 gM flavin N-oxide (RPMI only); 60 minutes
4, 5 and 6 are used as controls.

The cells are put in the incubator overnight to equilibrate in the flavin N-oxide. Then, they are counted just before photolysis and 10 mM of glutathione is added to each flask. They are photolyzed under air, using the 6 bulbs for the time mentioned above. Numbers 4 and 5 are wrapped in aluminum foil and kept outside the incubator for 60 minutes, so that they are standing in the same conditions of temperature and $CO_2$ concentration as the photolyzed flasks.

After photolysis, the cells are put back in the incubator and are counted at different time points (0, 1 h, 3 h, 4 h, 5 h, and 6 h after) to determine the moment they start dying.

We systematically vary the time of incubation of cells with the flavin N-oxide, the concentrations of the flavin N-oxide and glutathione, and the length of photolysis. By doing so, we can optimize our system to maximize the amount of specific killing due to the flavin N-oxide-nucleic acid photochemistry while minimizing the amount of nonspecific killing due to long-lived reactive oxygen species.

Example 4

Figure 3:
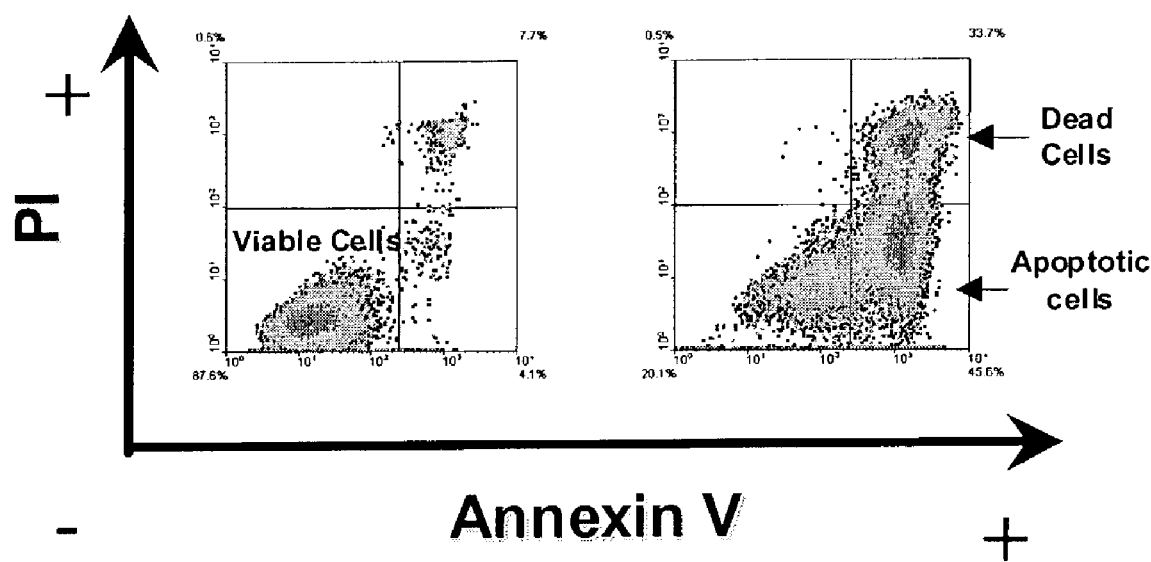
FIG. 3 is a representative example of the detection of apoptosis by the FACS method.

Cell Synchronization To maximize cell death by apoptosis, we wish to maximize the amount of flavin N-oxide bound to cellular DNA. During the S Phase, the cell is actively undergoing DNA synthesis. At the end of the S Phase, and just before cell division, it will contain two sets of DNA. It is proposed that cells will be most likely to bind the flavin N-oxide and to undergo the desired flavin N-oxide DNA photochemistry at this point of their cycle. Synchronizing the cells present in the sample will maximize the number of cells in S Phase, and so minimize the quantity of riboflavin N-oxide free in solution, that is, the risk of toxic death for the cells. Normally, cells proceed through four stages, known as the cell cycle. This process is schematically in FIG. 3.

Using a method described by Matherly[1] cell synchronization may be achieved with the drug aphidicolin, a DNA polymerase inhibitor. This drug prevents the cells from entering S-phase, the phase during which the cells replicate their DNA. Therefore, the cells accumulate at G1 phase, immediately prior to the start of S phase. These effects of aphidicolin are reversible; the cells return to normal cell-cycling soon after the drug is removed from the culture by washing. Thus, because all of the cells were synchronized together in G1, after removal of aphidicolin, they will proceed through S-phase together. Using flow cytometric analyis of propidium-iodine stained cells, as described by Krishan[2], we were able to determine the stage of cell cycle of the cultures:

We confirm that aphidicolin treatment synchronizes the cell cycle of the LCLs and significantly increases the proportion of cells in S-phase, with a peak at 6 hours after removal of aphidicolin from solution. Consequently, we hypothesize that treatment with aphidicolin will increase the effectiveness of specific killing via RBO-DNA photochemistry.

Example 5

Apoptosis Assay Apoptosis is a highly ordered genetically programmed cell death, which results in DNA degradation and nuclear condensation. It is activated by internal signals from the cell itself. In contrast, necrosis is death due to external injury to the cells. During apoptosis, cells may present signals, which may be used to induce significant immune responses. By taking advantage of this, one may potentially make vaccines by inducing apoptosis in cells. In order to more specifically describe the nature of cell death via RBO-DNA photochemistry, we use a technique described by Vermes[3] to detect the levels of apoptosis and necrosis of the cells via flow cytometry.

In the process of apoptosis, many changes occur in the cell. One of these changes is the translocation of phophatidylserine from the inside face of the plasma membrane to the outside. This change may be detected using a probe which has high affinity to phosphatidylserine called Annexin V. If Annexin V is complexed to a flurochrome, such as fluorescien isothiocyanate (FITC), it may be detected by a flow cytometer.

The translocation of phosphatidylserine also occurs as a result of necrotic cell death, however. One distinction between apoptotic cell death and necrotic cell death is that during the early stages of apoptosis, the outer membrane of the cell remains intact. After necrosis occurs, the membrane becomes leaky and allows substances to pass through. Consequently, one may use the fluorescent dye DNA stain propidium iodide (PI), which only passes through leaky membranes, as a membrane exclusion dye. In this way, only necrotic cells which allow PI to pass through will be PI positive, while normal and apoptotic cells will be PI negative.

Figure 4:
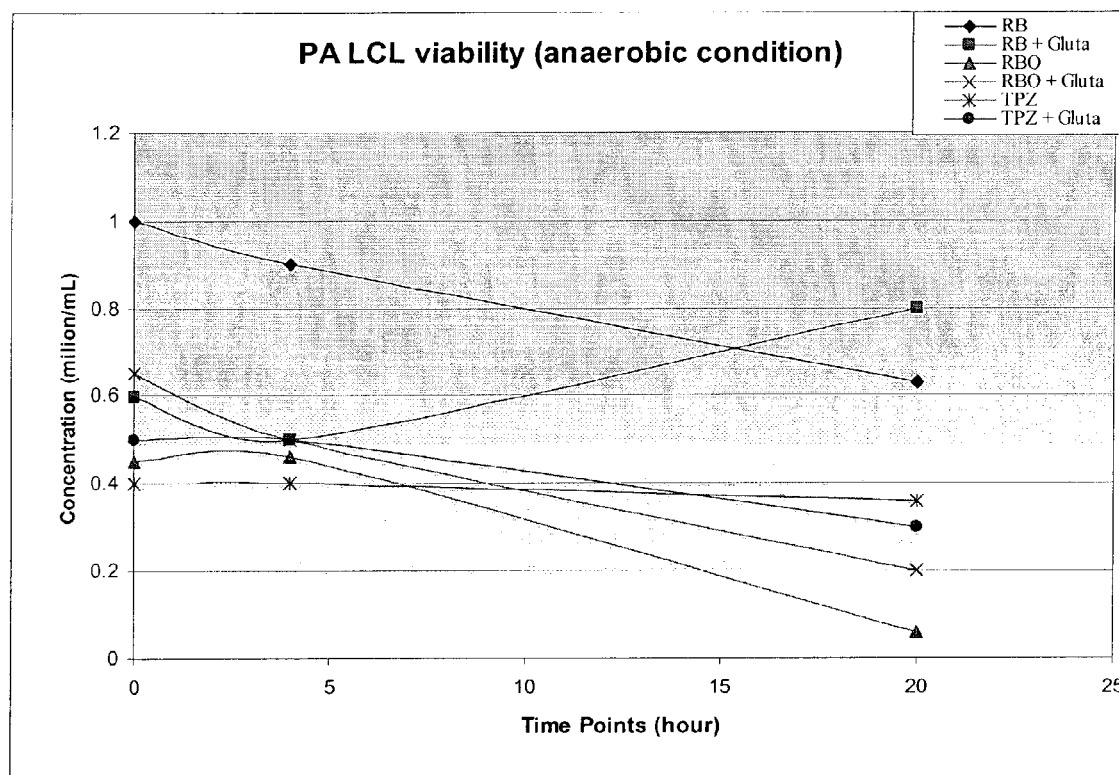
FIG. 4 shows the PA-Lymphoblastoid viability after treatment of the cells with riboflavin, riboflavin N-oxide and tirapazamine.

In summary, using Annexin V-PI staining, if cells are normal they will be negative for Annexin V and negative for PI staining. If cells are apoptotic, they will be positive for Annexin V and negative for PI. If cells are necrotic, they will be positive for both Annexin V and PI. This is represented by a flow cytometer as a density plot (note that each point represents a cell, whose X coordinate is a function of how much Annexin V is detected on the cell and whose Y coordinate is a function of how much PI is detected in the cell). An example of such a plot is shown in FIG. 4.

Using this assay, the susceptibility of synchronized and unsynchronized EBV infected human lymphoblastoid cells (LCLs) to flavin N-oxide-DNA photolysis may be compared. LCLs are treated with aphidicolin for 24 hours and then removed from culture. At this point, the flavin N-oxed is incubated with both the synchronized LCLs and unsynchronized controls for 6 hours, coinciding with maximal levels of synchronized cells in S-phase. The cells are then photolyzed for 1 hour. 8 hours after photolysis, the cells are analyzed using Annexin-PI staining for apoptosis. This experiment provides an indication that flavin N-oxed-DNA photolysis may be used to provoke immune responses.

Example 6

Generation of EBV-specific immune response in vitro using flavin N-oxide treated and photolyzed human LCLs Flavin N-oxide treated and photolyzed human LCLs may elicit an EBV-specific immune response in vitro when exposed to normal peripheral blood cells from a matching donor. Such an immune response may be created in vitro when EBV+ LCLs are irradiated and exposed to peripheral blood cells from the same donor. In our lab, we have a set of normal, healthy donors, for whom we have a readily available source of peripheral blood and an existing set of in vitro generated EBV+ transformed LCLs.

EBV-transformed LCLs obtained from several donors are treated with flavin N-oxide and subjected to photoradiation. The resulting flavin N-oxide-sensitized EBV-transformed LCLs are then contacted with peripheral blood cells obtained from the respective matching donor. In the immune response generated in this co-culture, we expect to see a proliferation of EBV-specific cytotoxic T Lymphocytes. These T cells are thought to expand from a population of existing EBV-specific memory T cells exist that respond by proliferating and gaining anti-tumor activity. This proliferation can be measured by quantitating the absolute number of cells generated in culture and analyzing these populations using flow cytometry to identify CD3+ CD8+ CD44+ T cells. These antigens identify T cells [CD3], Cytotoxic T cell subclass [CD8], and memory phenotype [CD44]. In addition to these antigens, we have molecular markers called MHC Class I tetramers that are specific for human MHC haplotypes that can identify T cells that are specific EBV-peptides. These tetramers are used in combination with standard flow cytometry and identify cytotoxic T cells as specific for EBV-antigens. In addition, anti-EBV tumor function of these cells may be demonstrated using two functional assays used in our lab: 1) ELIspot for gamma-interferon [Enzyme linked immunospot assay] and 2) Chromium release assay. The ELIspot assay measures gamma-interferon, a potent anti-tumor cytokine, released by T cells upon exposure to specific antigen. The Chromium assay measures the direct cytolytic activity of these T cells against labeled target.

An optimal immunogen is prepared when the flavin N-oxide is photolyzed in the presence of 10 mM glutathione, a physiological anti-oxidant. The glutathione neutralizes long-lived oxidants produced outside the cell. The cell is now damaged only by photolysis of intracellular flavin N-oxide. Photolysis of intracellular flavin N-oxide induces apoptosis, which leads to a more potent immunogen. The process is further enhanced by using synchronized cells to maximize the amount of flavin N-oxide bound to cellular DNA.

Example 7

PA-Lymphoblastoid Cell Line: Study of the effect of oxygen deprivation in the presence of 3 sensitizers Six solutions were prepared having the solutions and the cells from each of the 6 sets were "bubbled" with nitrogen separately for 15 minutes before being mixed.

| Time (hour) | 0 | 4 | 20 | |
|---|---|---|---|---|
| Riboflavin (RB) | 1 | 0.9 | 0.63 | million cells/mL |
| RB + gluta | 0.6 | 0.5 | 0.8 | million cells/mL |
| RBO | 0.45 | 0.46 | 0.06 | million cells/mL |
| RBO + gluta | 0.65 | 0.5 | 0.2 | million cells/mL |
| Tirapazamine (TPZ) | 0.4 | 0.4 | 0.36 | million cells/mL |
| TPZ + gluta | 0.5 | 0.5 | 0.3 | million cells/mL |

The results of this study are shown graphically in FIG. 5. This indicates high hypoxic toxicity of riboflavin N-oxide.

All documents referenced herein are incorporated by reference.

Although this invention has been described with respect to specific embodiments, the details of these embodiments are not to be construed as limitations.

REFERENCES

[1] Matherly L H, Schuetz J D, Westin E, Goldman I D. "A method for the synchronization of cultured cells with aphidicolin: application to the large-scale synchronization of L1210 cells and the study of the cell cycle regulation of thymidylate synthase and dihydrofolate reductase." *Anal Biochem.* 1989, 182(2), 338–45.

[2] Krishan A. "Rapid flow cytofluorometric analysis of mammalian cell cycle by propidium iodide staining." *J Cell Biol.* 1975, 66(1), 188–93.

[3] Vermes I, Haanen C, Steffens-Nakken H, Reutelingsperger C. "A novel assay for apoptosis. Flow cytometric detection of phosphatidylserine expression on early apoptotic cells using fluorescein labelled Annexin V." *J Immunol Methods.* Jul. 17, 1995; 184(1):39–51.

The invention claimed is:

1. A method of producing a cell preparation comprising a plurality of apoptotic EBV-transformed lymphocytes, comprising:
   a. infecting B lymphocytes with EBV to produce EBV-transformed B lymphocytes;
   b. incubating the EBV-transformed B lymphocytes in a medium comprising a flavin N-oxide under conditions which permit accumulation of flavin N-oxide in the EBV-transformed B lymphocytes;
   c. adding a non-toxic antioxidant to the medium; and
   d. exposing the lymphocytes to an activator wherein the flavin N-oxide is activated.

2. The method of claim 1 wherein the flavin N-oxide is of formula I:

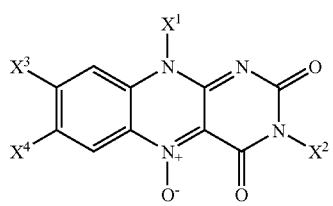

wherein
$X^1$ is selected from H, monosaccharides, substitited monosaccharides, mono, di, and tri-ethylene glycol, alcohol, and alkyl ammonium ion; and $X^2$, $X^3$, and $X^4$ can be the same or different and are selected from the group consisting of H, monosaccharides, substitited monosaccharides, glycol, alcohol, lower alkyl, and alkylene groups;

wherein $X^2$, $X^3$, and $X^4$ can be further substituted with monosaccharides, substitited monosaccharides, mono, di, and tri-ethylene glycol, alcohol, alkyl ammonium ion and combinations thereof.

3. The method of claim 2 wherein the flavin N-oxide is riboflavin N-oxide.

4. The method of claim 1 wherein the activator is electromagnetic radiation of an appropriate wavelength.

5. The method of claim 1 wherein the activator is an enzyme.

6. The method of claim 5 wherein the enzyme is a reducing enzyme present in the cell preparation.

7. The method of claim 1 wherein at least 25% of the EBV-transformed lymphocytes are in S phase when the flavin N-oxide is added to the medium.

8. A cell preparation produced by the method of claim 1, wherein the cell preparation comprises a plurality of apoptotic EBV-transformed B lymphocytes, the apoptotic EBV-transformed B lymphocytes comprise a DNA-flavin N-oxide adduct.

9. The cell preparation of claim 8 wherein the flavin N-oxide is of formula I:

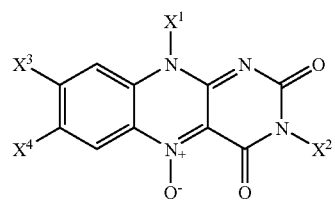

wherein
$X^1$ is selected from H, monosaccharides, substitited monosaccharides, mono, di, and tri-ethylene glycol, alcohol, and alkyl ammonium ion; and $X^2$, $X^3$, and $X^4$ can be the same or different and are selected from the group consisting of H, monosaccharides, substitited monosaccharides, glycol, alcohol, lower alkyl, and alkylene groups;

wherein $X^2$, $X^3$, and $X^4$ can be further substituted with monosaccharides, substitited monosaccharides, mono, di, and tri-ethylene glycol, alcohol, alkyl ammonium ion and combinations thereof.

10. The cell preparation of claim 9 wherein the flavin N-oxide is riboflavin N-oxide.

11. An apoptotic EBV-transformed B lymphocyte, wherein the apoptotic B lymphocyte comprises a DNA-flavin N-oxide adduct.

12. The apoptotic EBV-transformed B lymphocyte of claim 11 wherein the flavin N-oxide is of formula I:

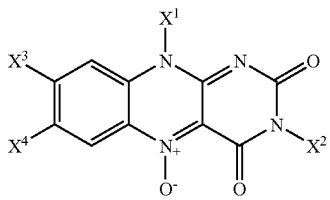

wherein
X¹ is selected from H, monosaccharides, substitited monosaccharides, mono, di, and tri-ethylene glycol, alcohol, and alkyl ammonium ion; and X², X³, and X⁴ can be the same or different and are selected from the group consisting of H, monosaccharides, substitited monosaccharides, glycol, alcohol, lower alkyl, and alkylene groups;

wherein X², X³, and X⁴ can be further substituted with monosaccharides, substitited monosaccharides, mono, di, and tri-ethylene glycol, alcohol, alkyl ammonium ion and combinations thereof.

13. The apoptotic EBV-transformed B lymphocyte of claim 12 wherein the flavin N-oxide is riboflavin N-oxide.

14. A method of eliciting production of EBV-specific T cells in a human subject, the method comprising administering a cell preparation to said subject, wherein the cell preparation comprises a plurality of apoptotic EBV-transformed B lymphocytes, the apoptotic EBV-transformed B lymphocytes comprise a DNA-flavin N-oxide adduct.

15. The method of claim 14 wherein the flavin N-oxide is of formula I:

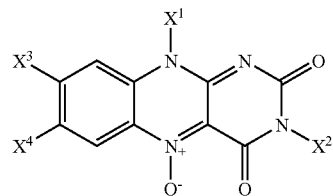

wherein
X¹ is selected from H, monosaccharides, substitited monosaccharides, mono, di, and tri-ethylene glycol, alcohol, and alkyl ammonium ion; and X², X³, and X⁴ can be the same or different and are selected from the group consisting of H, monosaccharides, substitited monosaccharides, glycol, alcohol, lower alkyl, and alkylene groups;

wherein X², X³, and X⁴ can be further substituted with monosaccharides, substitited monosaccharides, mono, di, and tri-ethylene glycol, alcohol, alkyl ammonium ion and combinations thereof.

16. The method of claim 15 wherein the flavin N-oxide is riboflavin N-oxide.

17. The method of claim 14 wherein the cell preparation is partially purified.

* * * * *